United States Patent [19]
Levin

[11] Patent Number: 5,976,170
[45] Date of Patent: Nov. 2, 1999

[54] BOWEL BLOCKAGE REMOVAL INSTRUMENT AND METHOD

[76] Inventor: Carl Levin, 5450 Whitley Park Ter. #809, Bethesda, Md. 20814

[21] Appl. No.: 08/879,054

[22] Filed: Jun. 19, 1997

Related U.S. Application Data

[60] Provisional application No. 60/034,562, Dec. 30, 1996.

[51] Int. Cl.⁶ .................................................. A61M 29/00
[52] U.S. Cl. ........................................... 606/197; 600/570
[58] Field of Search ............................. 600/570; 606/197, 606/191, 160, 159; 15/104.02, 104.03; 408/204, 205, 229

[56] References Cited

U.S. PATENT DOCUMENTS

| | | |
|---|---|---|
| 1,688,795 | 10/1928 | Aas . |
| 2,437,329 | 3/1948 | Moore . |
| 2,495,794 | 1/1950 | Weller . |
| 2,816,552 | 12/1957 | Hoffman . |
| 3,030,960 | 4/1962 | Turner et al. . |
| 3,931,820 | 1/1976 | Bucalo . |
| 4,236,520 | 12/1980 | Anderson ................................. 606/191 |
| 4,757,826 | 7/1988 | Abdulhay . |
| 5,131,402 | 7/1992 | Van Dooren . |
| 5,222,965 | 6/1993 | Haughton . |
| 5,342,384 | 8/1994 | Sugarbaker .............................. 606/191 |

*Primary Examiner*—Michael Buiz
*Assistant Examiner*—Julian W. Woo
*Attorney, Agent, or Firm*—Irvin A. Lavine

[57] ABSTRACT

An instrument for removing bowel blockage comprising a handle, and a probe element extending from the handle, the probe element being elongate, having a round or oval transverse cross-section, and having a rounded distal end, the handle being substantially imperforate, and the probe element being shaped to avoid injuring a patient, as by cutting. A method of safely removing bowel blockage comprises providing a probe element having a rounded distal end and rounded exterior and a handle at the proximal end of the probe element, inserting the distal end and at least some of the probe element into the rectum of a patient, and removing said probe element from the patient to permit evacuation of fecal matter through the anal canal.

14 Claims, 1 Drawing Sheet

BOWEL BLOCKAGE REMOVAL INSTRUMENT AND METHOD

RELATED APPLICATION

This application is based on and derives benefits from Provisional Application of Carl Levin, Bethesda, Md., Ser. No. 60/034,562, filed Dec. 30, 1996.

BACKGROUND OF THE INVENTION

This invention is directed to an instrument for overcoming bowel blockage by breaking up fecal matter above and near the anus, in the lower colon, to permit the ejection or evacuation of fecal matter in the normal manner.

A problem which occurs, particularly in the elderly and in some ill persons, is a blockage of the bowels. The fecal mass becomes impacted and normal passage of it through and out of the body does not occur. The fecal matter remains in the rectum and possibly in the colon, and is not passed through the anal canal.

Attempts to alleviate the problem by the use of enemas and suppositories have not proven effective in all cases.

The conventional attempt to alleviate the problem is for the physician or other attendant to insert a finger through the anus and into the rectum to attempt to dislodge the blockage. This procedure has not always been satisfactory, and appears to depend upon the physical characteristics of the patient, as well as that of the medical attendant. Even where it is successful, it is unpleasant.

A number of instruments have been provided in the prior art which include a probe-like element for insertion into the anus. Moore U.S. Pat. No. 2,437,329 discloses a surgical instrument for curetting, having a sharp edge which is rotated to collect fecal matter for bacteriologic and chemical examinations. Weller U.S. Pat. No. 2,495,794 is a rectal scraper having a cutting edge, the scraper being inserted into the rectum to scrape and collect for examination material within the patient for examination thereof.

Bucalo U.S. Pat. No. 3,931,820 discloses a lumen reamer which is inserted into a lumen having an elongate portion and a handle at the proximal end of the elongate portion, the elongate portion having openings or slots into it and having reaming edges which are to remove mucosa from a lumen.

Abdulhay U.S. Pat. No. 4,757,826 and Van Dooren U.S. Pat. No. 5,131,402 are biopsy instruments having cutting edges for removing specimens from the cervical region, each comprising a probe element having generally longitudinal or transverse cutting edges.

Hoffman U.S. Pat. No. 2,816,552 and Haughton U.S. Pat. No. 5,222,965 disclose probe-like instruments for insertion into teats, as of cattle, to obtain samples by incision for examination.

Aas U.S. Pat. No. 1,688,795 discloses a teat cannula and Turner et al U.S. Pat. No. 3,030,960 discloses a teat dilator; these comprise elongated, probe-like elements having a longitudinally extending passage which extends to and through the near or proximal end of the cannulas, and have a transverse passage intersecting the longitudinal passage.

SUMMARY OF THE INVENTION

The present invention provides an instrument to safely and effectively overcome the problem of bowel blockage in a ready and facile manner, while providing minimal discomfort to the patient. The present invention also provides a method for safely and effectively overcoming the problem of bowel blockage, while providing minimal discomfort to the patient.

The present invention provides an instrument which comprises a handle having extending from it a probe element which is elongate, and which is shaped to safely enter into the rectum and to engage and disturb impacted fecal matter therein in a safe manner. To that end, the probe element is of round or oval cross-section and has a rounded end, this construction being provided to enable a safe, non-injuring insertion and manipulation of the probe element. The probe element may have a longitudinally extending passage therein which is open to at least one surface of the probe element, and preferably provides a complete transverse passage through the probe element, so as to receive fecal matter therein, and remove it. This passage may be formed by spaced serrated walls having offset serrations to assist in breaking up the fecal matter, and has ends near the distal or far end and near the proximal or near end of the probe-like element.

A method is provided in which an instrument having a handle and an elongate probe element which is shaped to enable it to be safely inserted into and manipulated within the rectum, and possibly the colon, to impinge on and break up fecal matter, the probe element being additionally manipulated by imparting to it longitudinal, rotational and/ or lateral movement to effect disturbing and breaking up of impacted fecal matter Among the objects of the present invention are to provide an instrument which may be safely inserted into the bowel of a patient, and which disturbs or breaks up the fecal matter, without risk of injury to the patient, as by piercing or cutting the colon or other parts of the body of the patient.

Another object of the present invention is to provide such an instrument which may be readily manufactured of available materials and which may be provided for either disposal after a single use or for repeated usages.

Still another object of the present invention is to provide a method for removing fecal blockage in a safe manner, without risk of cutting or injuring the patient.

Other objects and many of the attendant advantages of the present invention will be readily understood from consideration of the following specification, drawings and claims.

Figure 1:
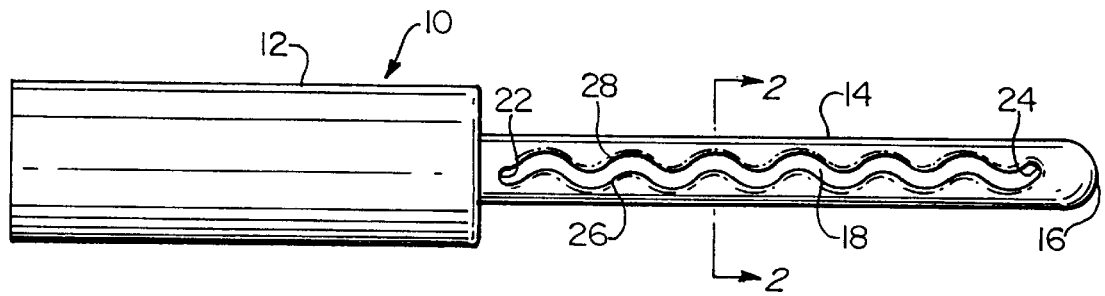
FIG. 1 is an elevational view of a bowel blockage removal instrument in accordance with the present invention.

The instrument 10 comprises a handle 12 of approximately three inches in length and of a diameter suitable to be grasped by the fingers of a person. Handle 12 is preferably solid. Extending from the handle 12 is a probe element 14 which is of suitable length, for example, four inches, and having a rounded distal end 16 to avoid cutting or tearing the colon or other portion of the patient. An opening 18 extends transversely into and preferably through the probe element 14 and longitudinally the length thereof. Opening 18 has ends 22 and 24 near the proximal and distal ends respectively of probe element 14, and is formed by preferably serrated walls 26 and 28 which are spaced apart and have offset serrations.

Figure 2:
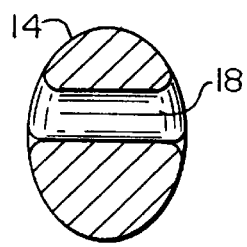
FIG. 2 is a cross-sectional view taken along the line 2—2 of FIG. 1.
Figure 3:
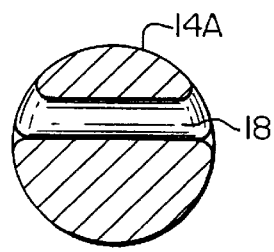
FIG. 3 is a view similar to FIG. 2, of an alternate embodiment.

As shown in FIG. 2, the probe element 14 may be oval in transverse cross-section, while in FIG. 3, the probe element 14A is round in transverse cross-section. To effect the above noted safe overcoming of bowel blockage, upon insertion of the probe element 14, each of the surfaces which form each entrance into the opening 18 is rounded, thereby avoiding cutting of the colon or other body part; all components which may come into contact with a part of the body will be seen to be shaped to avoid injury, as by not having a cutting action or a significant traumatizing action. The instrument 10 does not provide a passage through it for the evacuation of material from within the patient.

The instrument 10 may be of plastic, or other suitable material, and is either disposable or reusable.

In use, the rounded end 16 is inserted into the rectum, and engages an impacted fecal mass therein. The probe element 14 can be moved lengthwise, laterally and rotated as is necessary to disturb the fecal mass and break it up, to permit it to be thereafter ejected in the manner of a normal bowel movement after withdrawal of probe element 12 of the instrument 10. Some of the fecal matter may enter and remain in opening 18 and is removed, as by washing.

As described, the method of removing bowel blockage is by use of the instrument having a handle and a probe element which is configured to be inserted with safety to the patient into the rectum, and which is manipulated to disturb and dislodge impacted fecal matter, followed by removal of the probe element, with subsequent evacuation of fecal matter.

The claims and specification describe the invention presented, and the terms that are employed in the claims draw their meaning from the use of such terms in the specification. Some terms employed in the prior art may be broader in meaning than specifically employed herein. Whenever there is a question between the broader definition of such term as used in the prior art and the more specific use of the term herein, the more specific meaning is meant.

I claim:

1. Instrument for removing bowel blockage comprising:
   (a) a handle, and
   (b) a probe element extending from the handle, said probe element being elongated and shaped to be inserted into and through the anal canal without injury thereto and to the rectum,
   (c) said probe element having a transverse opening thereinto and extending along said probe element,
   (d) said transverse opening extending through said probe element and having at least one entrance thereinto from the exterior of said probe element,
   (e) each said entrance into said probe element being substantially rouned to avoid injury to the patient by cutting.

2. The instrument of claim 1, said transverse opening being provided by spaced serrated walls having offset serrations.

3. The instrument of claim 1, said transverse opening extending along substantially the entire length of said probe element, and having spaced ends.

4. The instrument of claim 1, said transverse opening being formed by spaced, offset serrated teeth.

5. The instrument of claim 1, said probe element having a rounded distal end.

6. The instrument of claim 1, said probe element being of round cross-section.

7. The instrument of claim 1, said probe element being of oval cross-section.

8. In an instrument for removing bowel blockage in a patient comprising,
   a probe element for insertion into the anal canal to engage and dislodge material therein;
   said probe element being elongated and having:
   a) a distal end shaped to avoid injury to the patient when inserted into the anal canal of the patient;
   b) an exterior surface shaped to avoid injury to the patient when introduced into and positioned in the anal canal of the patient, said exterior surface having at least one opening therethrough;
   c) said at least one opening being provided by surfaces for receiving material from within the anal canal, said exterior surface and said surfaces providing said at least one opening being substantially rounded to thereby avoid cutting of the patient.

9. The instrument of claim 8, wherein said distal end is rounded.

10. The instrument of claim 8, wherein said material receiving means comprises at least one transverse opening into said probe element and being spaced from said distal end thereof.

11. The instrument of claim 10, said transverse opening extending along said probe element.

12. The instrument of claim 11 wherein said transverse opening is provided with spaced serrated walls.

13. The instrument of claim 10, wherein said transverse opening is formed by spaced, offset serrated teeth.

14. The instrument of claim 10 wherein said transverse opening extends through said probe.

\* \* \* \* \*